United States Patent
Holappa et al.

(10) Patent No.: US 7,838,643 B2
(45) Date of Patent: Nov. 23, 2010

(54) QUATERNARY POLYMERS

(75) Inventors: Jukka Holappa, Kuopio (FI); Tomi Järvinen, Kuopio (FI); Tapio Nevalainen, Hiltulanlahti (FI); Jouko Savolainen, Kuopio (FI); Rustam Safin, Kuopio (FI)

(73) Assignee: Archimedes Development Limited, Nottingham (GB)

( * ) Notice: Subject to any disclaimer, the term of this patent is extended or adjusted under 35 U.S.C. 154(b) by 96 days.

(21) Appl. No.: 11/991,784

(22) PCT Filed: Aug. 31, 2006

(86) PCT No.: PCT/FI2006/050373

§ 371 (c)(1),
(2), (4) Date: Apr. 14, 2008

(87) PCT Pub. No.: WO2007/034032

PCT Pub. Date: Mar. 29, 2007

(65) Prior Publication Data

US 2009/0118480 A1     May 7, 2009

(30) Foreign Application Priority Data

Sep. 20, 2005   (FI) ................................. 20055503

(51) Int. Cl.
C07H 19/04 (2006.01)
C07H 19/048 (2006.01)
C07H 19/052 (2006.01)
C07H 5/06 (2006.01)

(52) U.S. Cl. ....................................................... 536/20
(58) Field of Classification Search ....................... None
See application file for complete search history.

(56) References Cited

U.S. PATENT DOCUMENTS 5,349,089 A     9/1994 Trzasko et al.
5,463,034 A *  10/1995 Buysch et al. ............. 536/17.2

FOREIGN PATENT DOCUMENTS

EP          0406837 B1     1/1991

OTHER PUBLICATIONS

Li, H. et al., Colloids and Surfaces A: Physiochem. Eng. Aspects "Effect of molecular weight and degree of substitution of quaternary chitosan on its adsorption and flocculation properties for potential retention-aids in alkaline papermaking", vol. 242, pp. 1-8 (2004).*
Holappa et al., "N-chloroacyl-6-O-triphenylmethylchitosans: Useful Intermediates for Synthetic Modifications of Chitosan", Biomacromolecules 2005, 6(2) 858-863, whole document.
Chun-Ho Kim et al., "Synthesis and Antibacterial Activity of Water-soluble Chitin Derivatives", Polymers for Advanced Technologies vol. 8 (1997), pp. 319-325.

* cited by examiner

Primary Examiner—Shaojia Anna Jiang
Assistant Examiner—Bahar Schmidtmann
(74) Attorney, Agent, or Firm—Panitch Schwarze Belisario & Nadel LLP

(57) ABSTRACT

The present invention relates to novel quaternized polymers, especially of chitin/chitosan type, and to carbohydrate polymers carrying quaternized ammonium groups, especially piperazinium groups. Such polymers are characterized i.a. by improved solubility characteristics.

11 Claims, No Drawings

QUATERNARY POLYMERS

FIELD OF THE INVENTION

This invention is aimed at novel quaternary polymers and methods for adding quaternary ammonium moieties into oligomers or polymers, such as any natural, semi-synthetic or synthetic polymer, preferably to chitosan and chitin, via different covalently bonded spacers. The said quaternary ammonium polymer derivatives have enhanced aqueous solubility, usability and activity in many industrial applications, e.g., in pharmaceutical applications, in cosmetics, food science, water purification, pulp and paper industry, and in the textile industry. One or more quaternary moieties can be inserted into a monomer unit of the polymer. This invention is also aimed at mono-ja di-quaternary piperazinium acids usable in the preparation of the said polymers, as well as to methods of their preparation.

BACKGROUND OF THE INVENTION

Chitosan (poly-1,4-β-D-glucosamine) is a non-toxic (Journal of Biomedical Material Research 59, 2002, 585) and biodegradable (Biomaterials 20, 1999, 175) polysaccharide that is derived from chitin by deacetylation in basic conditions. The term chitosan is used to describe a wide variety of heteropolymers of glucosamine and N-acetylglucosamine with varying degrees of deacetylation and molecular weights. Chitosan has many potential applications in various fields, e.g., in pharmacy and medicine (Drug Development and Industrial Pharmacy 24, 1998, 979; Pharmaceutical Research 15, 1998, 1326; S.T.P. Pharma Science 10, 2000, 5), food science (International Dairy Journal 14, 2004, 273; Agro Food Industry Hi-Tech 14, 2003, 39), water purification (Water Research 34, 2000, 1503), pulp and paper industry (Journal of Applied Polymer Science 91, 2004, 2642), and in the textile industry (Journal of Macromolecular Science Polymer Reviews C43, 2003, 223).

The main obstacle to the use of chitosan in different applications is poor solubility properties, especially the poor aqueous solubility. The poor solubility of chitin and chitosan is due to strong intra- and intermolecular hydrogen bonding leading to highly crystallized structures. Chitosan dissolves only in acidic aqueous solutions due to the protonation of the amino groups in the polymer. Chitosan is poorly soluble in all common organic solvents. Chitosan becomes soluble in water when the degree of deacetylation is approximately 50% due to unfavourable conformation to form intermolecular hydrogen bonds (Biomacromolecules 1, 2000, 609). Various chitin and chitosan derivatives have been designed and synthesized, mainly to improve the solubility properties of chitosan (Progress in Polymer Science 26, 2001, 1921; Progress in Polymer Science 29, 2004, 887). Anionic water soluble chitosan derivatives are carboxyl acid derivatives (International Journal of Biological Macromolecules 14, 1992, 122; European Polymer Journal 39, 2003, 1629), phosphates (Carbohydrate Polymers 44, 2001, 1) and sulfates (Carbohydrate Research 302, 1997, 7). Other water soluble chitosan derivatives are poly(ethylene glycolated) derivatives (Carbohydrate Polymers 36, 1998, 49).

Important water soluble chitosan derivatives are derivatives with a quaternary ammonium moiety. These derivatives have two major advantages over the parent chitosan: (1) they are water-soluble on a wide pH-range including neutral and basic conditions, and (2) they have a permanent positive charge on the polymer backbone. The polycationic nature is commonly regarded to be responsible for the unique properties and activity of chitosan. Quaternary chitosan derivatives can be prepared either by quaternizing the amino group already present in the polymer or by adding a quaternary ammonium moiety or moieties. Synthesis of (N,N,N)-trimethylchitosan has been widely studied and reported (Carbohydrate Polymers 5, 1985, 297; International Journal of Biological Macromolecules 8, 1986, 105; Carbohydrate Polymers 24, 1994, 209; Carbohydrate Polymers 36, 1998, 157; Drug Development and Industrial Pharmacy 27, 2001, 373). The pharmaceutical properties of (N,N,N)-trimethylchitosan have been widely studied (e.g., European Journal of Pharmaceutics and Biopharmaceutics 58, 2004, 225; Biomaterials 23, 2002, 153; Carbohydrate Research 333, 2001, 1). However, well-defined uniform chitosan derivative structures cannot be obtained by direct methylation if the hydroxyl groups are not protected. Hydroxyl groups in the polymer, i.e., the primary hydroxyl at position 6 and the secondary hydroxyl at position 3, are also methylated. High degrees of quaternization cannot be obtained without the total O-methylation of the polysaccharide (Carbohydrate Polymers 36, 1998, 157).

The amino group in chitosan has also been quaternized by first reductively alkylating it with aldehydes to form imines, followed by reduction to obtain N-alkyl derivatives. These alkyl derivatives have been further quaternized with alkyl iodides (Polymer Bulletin 38, 1997, 387; Carbohydrate Research 333, 2001, 1; European Polymer Journal 40, 2004, 1355). Uragami and co-workers have crosslinked (N,N,N)-trimethylchitosan with various crosslinking agents, e.g., with tetraethoxysilane (Biomacromolecules 5, 2004, 1567) and with diethylene glycoldiglycidylether (Macromolecular Chemistry and Physics 203, 2002, 1162). Murata et al. quaternized some of the amino groups in galactose derivative of chitosan (Carbohydrate Polymers 29, 1996, 69; Carbohydrate Polymers 32, 1997, 105). Ucheqbu et al. prepared a quaternary ammonium palmitoyl chitosan to obtain a polysoap for drug delivery (International Journal of Pharmaceutics 224, 185-199). However, all these share the problem with (N,N,N)-trimethylchitosan, i.e., uniform structures cannot be obtained due to methylation of the hydroxyl groups of the polymer during the synthetic procedure.

The quaternary ammonium moiety can be inserted into polymer structures via various spacers. N-[(2-hydroxy-3-trimethylammonium)propyl]chitosan chloride can be obtained by reacting chitosan with glycidyltrimethylammonium chloride (Biomaterials 24, 2003, 5015; Carbohydrate Research 339, 2004, 313; Coloration Technology 120, 2004, 108; Colloids and Surfaces A: Physicochemical Engineering Aspects 242, 2004, 1; Polymer Journal 32, 2000, 334; International Journal of Biological Macromolecules 34, 2004, 121-126). This N-[(2-hydroxy-3-trimethylammonium)propyl]chitosan has been studied for different applications such as in cosmetics (e.g., U.S. Pat. No. 4,772,690; U.S. Pat. No. 4,822,598; U.S. Pat. No. 4,976,952). This derivative with varying lengths of alkyl chains attached to quaternary nitrogen has also been described as an antimicrobial agent (U.S. Pat. No. 6,306,835) and as a cholesterol lowering agent (WO9206136).

Another example of quaternary chitosan derivatives is N-betainate chitosan (Macromolecules 37, 2004, 2784; S.T.P. Pharma Sciences 8, 1998, 291). Lee et al. prepared quaternized diaminoalkylchitosans to obtain chitosan derivatives having two quaternary moieties (Bioscience Biotechnology and Biochemistry 63, 1999, 833; Bioorganic & Medicinal Chemistry Letters 12, 2002, 2949). Chun-Ho et al. prepared and studied the antibacterial activity of (triethylaminoethyl) chitin (Polymers for Advanced Technologies 8, 1997, 319). Suzuki et al. prepared N-p-(N-methylpyridinio)methylated chitosan and N-4-[(3-trimethylammonio)propaxy]benzylated chitosan and studied the electric resistance of these materials (Polymer Journal 32, 2000, 334).

Other polysaccharides have also been modified by inserting a quaternary ammonium moiety, e.g., cellulose (Macromolecular Materials and Engineering 286, 2001, 267) and starch (International Journal of Biological Macromolecules 31, 2003, 123). There are several commercial producers of these water-soluble quaternary derivatives of starch and cellulose. Tsai et al. reported alkylation of starch with monoquaternary 4,4-diethyl-1-(chloroethyl)piperazinium chloride hydrochloride and with diquaternary 1-glycidyl-1,4,4-trimethylpiperazinium dichloride (U.S. Pat. No. 5,349,089). However, no physicochemical properties, e.g., aqueous solubility of these alkylated starch derivatives were reported.

We have earlier prepared non-quaternary N-methylpiperazine derivatives of chitosan, but these were only relatively more soluble in water than the parent chitosan (Biomacromolecules 6, 2005, 858). By preparing quaternary piperazine derivatives we can obtain derivatives that are highly water-soluble on a wide pH range. However, quaternary piperazine derivatives cannot be prepared directly from these non-quaternary chitosan derivatives. To obtain a quaternary nitrogen atom one needs harsh reaction conditions usually with a large excess of the alkylating reagent. It is impossible to obtain well-defined chitosan derivatives by alkylating the non-quaternary chitosan derivatives, since this approach would result in a heteropolymer with both diquaternary and monoquaternary piperazine moieties in monomers. Also the hydroxyl groups in chitosan would be alkylated. The alkylation of hydroxyl groups of chitosan have shown to decrease the aqueous solubility of chitosan, e.g., Sieval et al. reported that the quaternary chitosan derivatives with high degrees of O-methylation were insoluble in water, even with high degree of quaternization (Carbohydrate Polymers 36, 1998, 157). This also proves that quaternary chitosan derivatives, even with high degree of quaternization, are not necessary water-soluble.

SUMMARY OF THE INVENTION

According to a first aspect the present invention is directed to a novel group of polymers represented by the following general formula:

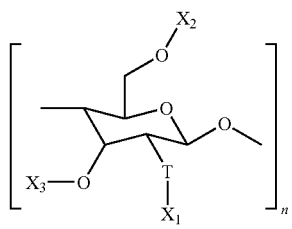

(I)

wherein

T is NH or O, $X_1$, $X_2$ and $X_3$ are independently:

H or

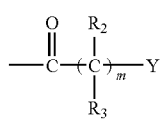

in the case of T being NH (i.e. chitin and chitosan), $X_1$, $X_2$ and $X_3$ can also be

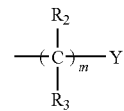

and, in addition, $X_1$ can also be:

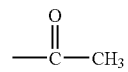

wherein $R_2$ and $R_3$ are independently H or a linear or branched, substituted or unsubstituted alkyl chain with 1 to 6 carbon atoms and m is an integer from 1 to 12, Y is a quaternary ammonium moiety selected from piperazine moieties having the formula

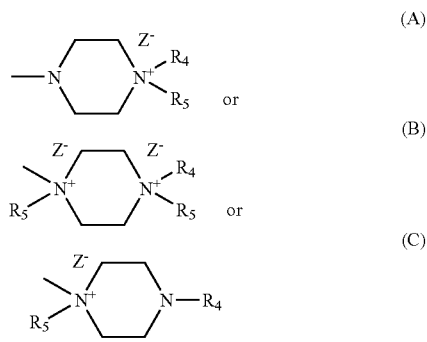

(A)

(B)

(C)

or selected from the groups

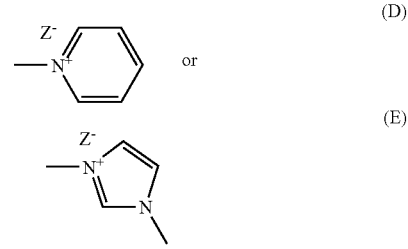

(D)

(E)

wherein $R_4$ and $R_5$ are independently a linear or branched, substituted or unsubstituted alkyl chain with 1 to 6 carbon atoms, $Z^-$ is a negatively charged counter ion, preferably selected from the group consisting of $Cl^-$, $Br^-$, $I^-$, $OH^-$, $R_1COO^-$, $R_1SO_4^-$, wherein $R_1$ is H or an alkyl group with 1 to 6 carbon atoms or an aromatic moiety, whereby the degree of substitution (ds) of the quaternary substituent for the total of the groups $X_1$, $X_2$ and $X_3$ is at least 0.01, n is the degree of polymerization, and can be an integer from 2-100000, with the proviso that when T is O, Y can only have the meaning of a group of the formula (A), (B), (C) or (E) as defined.

The invention is also directed to methods of preparing the novel quaternary polymers, as well as to mono- and di-quaternary piperazinium acids of the formula

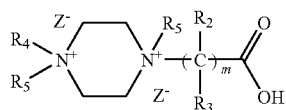
VIIIa

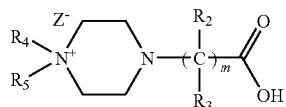
VIIIb wherein $R_2$, $R_3$, $R_4$, $R_5$, m and $Z^-$ are as defined above, as well as base salts thereof, as well as to methods for preparing the same.

According to a further aspect, the invention is directed to novel derivatives of any carbohydrate polymer, or any other natural, semisynthetic or synthetic polymer having a hydroxyl or amino group substituted with a quaternary group as defined above for $X_1$, $X_2$ or $X_3$, wherein Y is a mono- or di-quaternized piperazine group of the formula (A), (B), (C) or (E) as defined above.

DETAILED DESCRIPTION OF THE INVENTION

The monomer units of the quaternary polymers can be independently substituted by the groups $X_1$, $X_2$ and $X_3$. Thus there can be different monomers in the polymers, i.e., one or more of the functional groups in some of the monomer units are substituted with quaternary groups (i.e. $X_1$, $X_2$ and/or $X_3$=

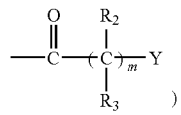
)

and some are unsubstituted (i.e., $X_1$, $X_2$ and $X_3$H). In case T is NH (i.e. chitin and chitosan), $X_1$, $X_2$ and $X_3$ can also be

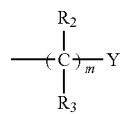

and, in addition, $X_1$ can also be:

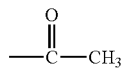

These different monomers can be evenly distributed within the polymer structure or they can also form block structures. The degree of substitution of the quaternary substituent

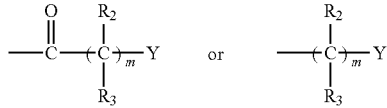

in the polymer structure can be from 0 to 1 independently for each one of the groups $X_1$, $X_2$ and $X_3$, however, the overall degree of substitution for all the groups $X_1$, $X_2$ and $X_3$ together being at least 0.01, in order to provide for a content of the necessary quaternary substituent in the polymer. The maximum degree of substitution is 3, in which case there are three quaternary substituents per monomer in each monomer unit of the polymer. A degree of substitution of, for example, 0.01 for a substituent means that there is on an average 1 of said substituents per 100 monomer units in the polymer, and a degree of substitution of 1 means that there is on an average one substituent in each monomer unit in the polymer. Typically the degree of substitution for the quaternary group will lie in the range of 0.05 to 1. However, the optimal degree of substitution depends on the applications in which these quaternary polymer derivatives are used.

In the above formula, an alkyl group in the meaning of $R_1$ to $R_5$ contains 1 to 6 carbon atoms, preferably 1 to 4 carbon atoms, and preferably in a straight chain. One advantageous alkyl group is the methyl group. In the above formula, $R_2$ and $R_3$ are preferably hydrogen. The said alkyl group can be unsubstituted or substituted, whereby the substituents can be lower alkoxy (1-3 carbon atoms), hydroxy or halogen.

Within the context of the invention, an aromatic group is advantageously a phenyl group, a benzyl group or a naphtyl group, which may be unsubstituted or substituted with one to three substituents selected from lower alkyl or lower alkoxy (1-3 carbon atoms) or halogen.

In the above formula, n is the degree of polymerization, and can be an integer giving a polymer with 2-100000 structural units, i.e., the polymer can range from a dimer with two monomers to a polymer with a molecular weight of at least 10000000.

A preferred group of polymers are those, wherein T is NH, $X_1$, $X_2$ and $X_3$ are as defined above, wherein Y is one of the groups having the formulas (A), (B) or (C), and wherein the degree of substitution of the quaternary group is from 0.01 to 1, preferably 0.05 to 1.

A preferred group of polymer derivatives is formed by those having the formula (I) above wherein T is NH, $X_2$ and $X_3$ are hydrogen and $X_1$ is hydrogen, acetyl or a group containing a quaternary ammonium moiety, especially one of the groups having the formulas (A) to (E), and in particular the formulas (A), (B) or (C). In such a case the degree of substitution of the quaternary group will range from 0.01 to 1, being preferably 0.05 to 1.

According to a preferred embodiment, when the polymer backbone is starch, cellulose, pullulan or dextran, the general formula of the polymer derivative is:

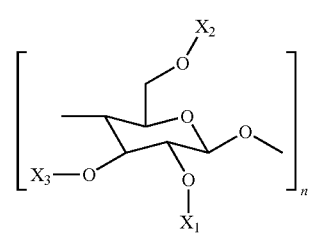
(II)

wherein $X_1$, $X_2$, $X_3$ have the formulas presented above, wherein Y has the meaning of a quaternary group of the formula (A), (B), (C) or (E), and $R_2$, $R_3$, $R_4$, $R_5$, $Z^-$, m and n are as above defined, and the degree of substitution of the quaternary group in the polymer is from 0.01 to 1.

As in the case of chitin and chitosan, there can be different monomer units in the said polymers of formula (II), i.e., in any monomer unit one or more of the functional groups can be substituted (i.e., $X_1$, $X_2$, and/or $X_3=$

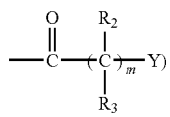

or the functional groups can be unsubstituted (i.e., $X_1$, $X_2$, and $X_3$=H). The different monomer units can be evenly distributed or they can also form block structures within the polymer structure. The degree of substitution of the quaternary groups is as described above for the chitin and chitosan structures.

The present invention is also directed to mono- and di-quaternary piperazinium acids of the formulas VIIIa and VIIIb given below, as well as to methods for their preparation. These type of moieties have been built in e.g. into prodrug molecules to enhance the aqueous solubility of the parent compound (Pharmaceutical Research 13, 1996, 469). The reported quaternary piperazinium derivatives have been synthesized by first attaching the secondary or tertiary piperazine moiety to a target compound followed by quaternization with alkyl halides. Unfortunately, this strategy often leads to mixtures of products, especially when the parent molecule has numerous functional groups, leading to the need for laborious separation of mono- and diquaternary piperazinium salts and side-products.

The novel mono- and di-quaternary piperazinium acids have the formulas

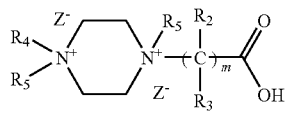

VIIIa

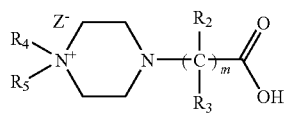

VIIIb wherein $R_2$, $R_3$, $R_4$, $R_5$, m and $Z^-$ are as hereinabove defined and their salts.

Appropriate base salt forms comprise, for example, the ammonium salts, the alkali and earth alkaline metal salts, e.g. the lithium, sodium, potassium, magnesium, calcium salts and the like, salts with organic bases, e.g. trimethylamine, triethylamine, triethanolamine, N-methyl-N,N-diethanolamine, ethylenediamine, and salts with amino acids such as, for example, arginine, lysine and the like.

The said piperazinium acids are prepared by reacting a compound having the formula

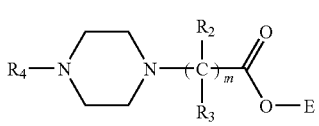

X wherein $R_2$, $R_3$, $R_4$ and m have the meaning given above and E is hydrogen or any commonly used protecting group for the carboxyl moiety (Green T W, Wuts P G M: Protection for the carboxyl group. Protective groups in Organic Synthesis 3rd edition. Pages 369-453. John Wiley & Sons 1999), preferably ethyl, which can be removed, for example by hydrolysis to form the corresponding acid, with a quaternizing compound corresponding to the group $R_5$, such as a suitable alkyl halide, alkyl fluorosulfonate, dialkyl sulfate, alkyl tosylate, or alkyl mesylate, to form a mixture of the compounds having the formulas

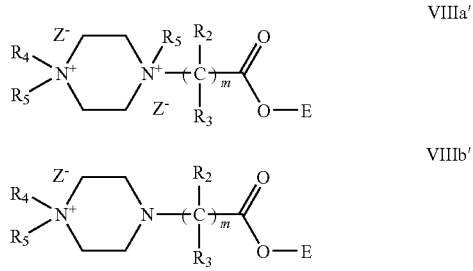

VIIIa'

VIIIb' wherein $R_2$, $R_3$, $R_4$, $R_5$, m and E have the meanings given above, thereafter separating the compounds, and, if necessary, converting the so separated compounds into their corresponding acids, and optionally converting the acid obtained into a salt as defined above. The separation of the two compounds can preferably be carried out by precipitating one of the compounds, preferably the diquaternary piperazinium acid (i.e., VIIIa'), by a suitable choice of solvent, whereby the other compound will remain in solution.

Suitable solvents for use are, e.g., acetonitrile, pyridine, t-butanol, 1-butanol, methyl ethylketone, 2-propanol, 1-propanol, acetone, ethanol, methanol, nitrobenzene, dimethylformamide, ethylene glycol, DMSO and water. The person skilled in the art can for example based on the dielectricity constants of the solvents easily select the solvents, in which e.g. the di-quaternized compound will precipitate, and the mono-quaternized compound will remain in solution, wherefrom it can be recovered, for example by evaporation.

In the following, when the term chitosan is used, it is intended to mean both chitin and chitosan.

The chitin and chitosan derivatives according to the invention containing a quaternary ammonium group in $X_1$, $X_2$ and/or $X_3$ can generally be prepared by reacting a chitin or chitosan derivative having a free amino or hydroxyl group, whereby the remaining reactive groups are optionally protected, with a compound having the formula V'

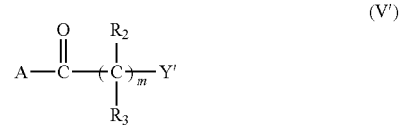

(V')

wherein A is an activating group, Y' is a suitable leaving group or is a quaternary ammonium group Y, $R_2$, $R_3$, m and Y are as hereinabove defined, or with a compound having the formula III

(III)

wherein L is a leaving group, and Y' is either a quaternary ammonium group Y or a leaving group, and $R_2$, $R_3$, m and Y are as above defined, whereby L is as good a; or a better, or more reactive leaving group, as compared to a leaving group Y', and when an intermediate compound containing a leaving group Y' is obtained, the intermediate is further reacted with a tertiary or aromatic amine corresponding to the quaternary ammonium group Y, to yield the desired quaternary polymer, and removing any protecting groups.

In the formula III, L can be for example triflate, tosylate, mesylate, bromide or iodide, and Y' as a leaving group can be for example chloride.

According to the invention, a compound obtained wherein $X_1$, $X_2$ and/or $X_3$ have the meaning of hydrogen, can be converted to a compound wherein said $X_1$, $X_2$ and/or $X_3$ are different from hydrogen, by reacting the same with a compound of the formula III or V', wherein the symbols have the meaning as defined, and reacting an intermediate so obtained containing a leaving group Y', with a tertiary or aromatic amine corresponding to the quaternary ammonium group Y, and removing any protecting group optionally used in the reaction.

According to the invention, for the preparation of a compound containing a group $X_2$ and/or $X_3$ which is different from hydrogen and wherein $X_1$ is different from a group containing a quaternizing group, a chitin or chitosan derivative, wherein the amino group is protected and one or both of the hydroxyl groups are unprotected, is reacted with a compound of the formula III or V', wherein the symbols have the meaning as defined, and reacting any intermediate obtained in which Y' is a leaving group, with a tertiary or aromatic amine corresponding to the quaternary ammonium group Y and removing any protecting groups.

A chitin or chitosan derivative according to the invention, wherein $X_1$ is a group as defined above containing a quaternary ammonium group, can be prepared for example by reacting a chitin or chitosan polymer in which the hydroxyl groups in the 3 and/or 6-positions are optionally protected, and having a free amino group in one or more of the monomer units of the chitosan polymer, with a compound of the formula III or V' as defined above, and then in a second step, if necessary, with a tertiary or aromatic amine corresponding to the quaternary ammonium group Y and removing any protecting groups.

According to an embodiment, polymers in which $X_1$ is a group as defined above containing a quaternary ammonium group and $X_2$ and $X_3$ are hydrogen can be prepared by reacting a chitin or chitosan polymer in which the hydroxyl groups in the 3 and/or 6-positions are optionally protected, and the amino group in one or more of the monomer units of the polymer carries an alkyl or alkyloxy group corresponding to the group $X_1$, wherein the group Y is replaced by a suitable leaving group, with a tertiary or aromatic amine corresponding to the quaternary ammonium group Y, and removing any protecting groups.

According to a second embodiment, for the preparation of polymers having an amino group substituted with a group $X_1$ containing a quaternary ammonium group, a chitin or chitosan polymer having a free amino group and in which the hydroxyl groups in the 3 and/or 6-positions are optionally protected, is reacted with a compound having the formula III or V' as defined above, and when Y' in the formula III or V' is a leaving group, reacting the so obtained intermediate compound with a tertiary or aromatic amine corresponding to the group Y, and removing any protecting groups.

Examples of such methods are illustrated by the method A or the method B, which are depicted in Schemes I and II, respectively. Scheme I illustrates the reaction for a monomer unit in the starting polymer Ia wherein the amino group has been substituted with an alkyl or alkyloxy group carrying a leaving group Y'.

Method A

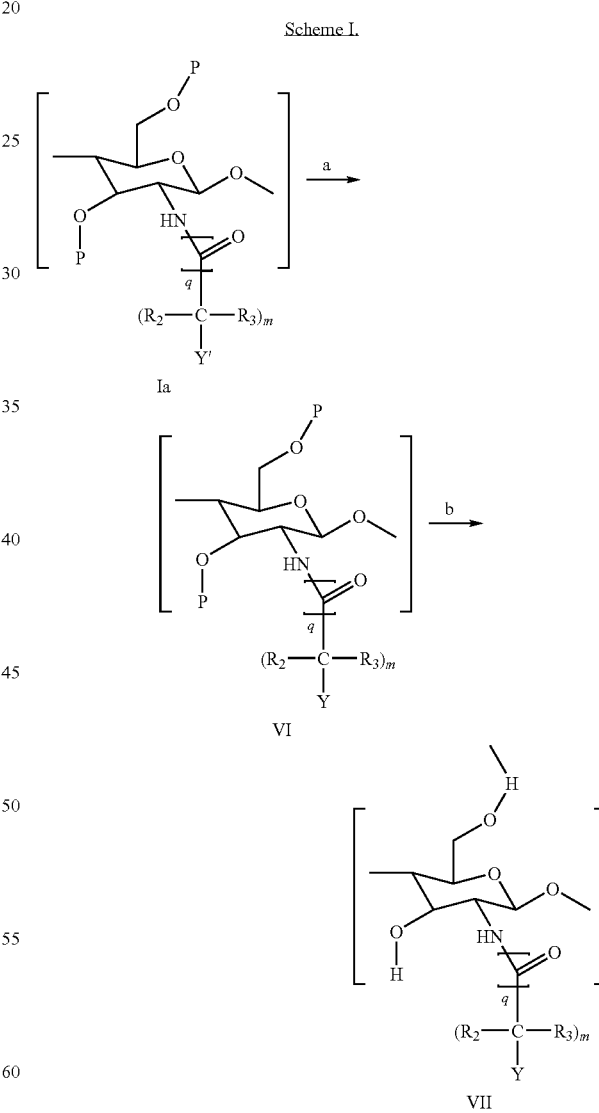

Thus the quaternary ammonium polymers of the formula VII can be prepared by a substitution reaction of the polymer Ia with a tertiary or aromatic amine corresponding to the group Y. In the formula, P is independently H or a protecting group. The protecting group may be e.g. a triphenylmethyl group (Tr), benzyl, p-nitrobenzyl, p-methoxybenzyl, t-butyl, allyl or acetyl group. A particularly preferred protecting group for use in this invention is the triphenylmethyl (Tr) group; Y' is a suitable leaving group, e.g., chlorine, tosylate, iodine etc., preferably bromine or chlorine. $R_2$ and $R_3$ are as above defined, and q is 0 or 1, indicating the absence (q=0) or presence (q=1) of a keto group in the amino substituent.

In a first step (a) the protected or unprotected intermediate Ia is reacted with any tertiary or aromatic amine corresponding to the quaternary ammonium group containing moiety Y, preferably with 1,4-dimethylpiperazine, pyridine or 1-methylimidazole, to yield the quaternary polymer VI.

In a second step (b) the possible protecting groups are removed by reactions such as reduction with hydrogenolysis (for instance, in the presence of a palladium black catalyst), treatment with a hydrohalide acid such as a hydrochloric, hydrobromic, hydrofluoric or hydroiodic acid, or treatment with trifluoroacetic acid. Preferably 1M hydrochloric acid is used.

Method B

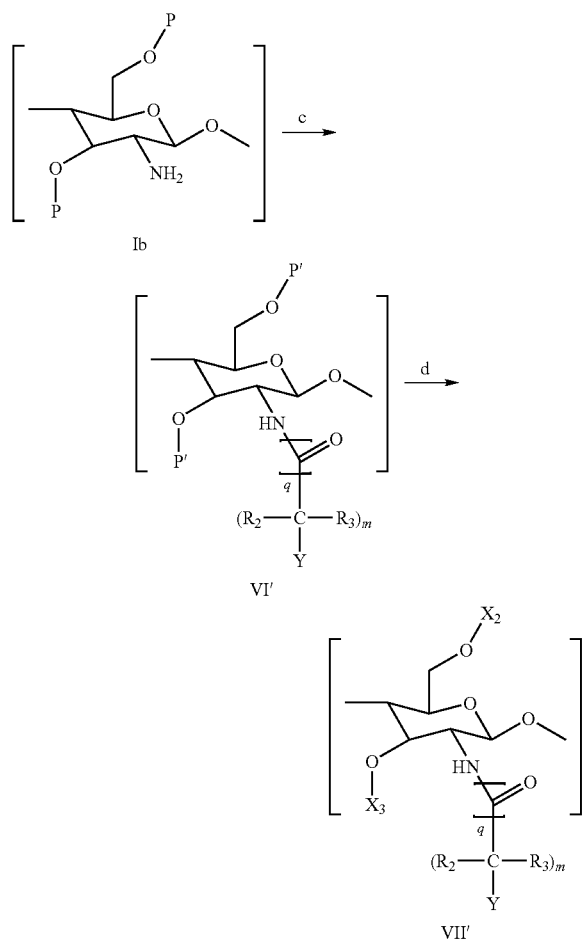

The scheme II shows the reaction of a monomer unit in the polymer 1b containing a free amino group. The quaternary ammonium polymers of formula VII', wherein $X_2$ and $X_3$ are hydrogen or a quaternary group, and the other symbols have the meanings as defined, can be prepared by condensing the amino group of the intermediate 1b with a compound having the formula V' or III as defined above, wherein Y' is a quaternary ammonium group Y, preferably with a mono- or di-quaternary piperazium acid of the following formula,

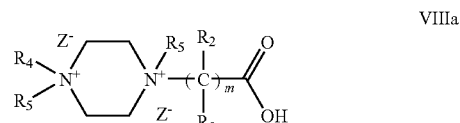

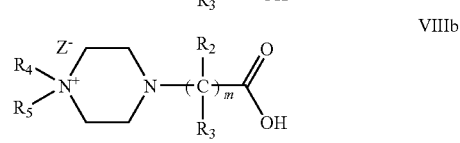

wherein $R_2$, $R_3$, $R_4$, $R_5$, m and $Z^-$ are as hereinabove defined.

In the formula Ib, P is independently H or a protecting group as hereinabove defined. In the step c, the compound VI' is formed where P' has the meaning of a protecting group, hydrogen or $X_2$ or $X_3$. The reaction with the compound V' is favorably effected in the presence of an activating agent, such as N,N'-dicyclohexylcarbodiimide and 1-hydroxybenzotriazole. The reaction is carried out in an inert solvent such as in aliphatic or aromatic, preferably halogenated hydrocarbons, alcohols, ethers, glycols, amides such as formamide, dimethyl formamide or acetamide, N-methylpyrrolidone or phosphoric acid tris-(dimethylamide), acetonitrile, dimethyl sulphoxide and tetramethylene sulphone. Water can also be used as a solvent.

In a second step (d) the possible protecting groups are removed as hereinabove defined.

When the protecting groups (P) are not used, it is possible that one or more of the functional groups $X_2$ and $X_3$ in chitin and chitosan are also substituted with a quaternary group, i.e., the degree of substitution for the groups $X_2$, and $X_3$ is independently 0-1, as discussed earlier.

Protection groups are needed, when the quaternary substituents are to be attached regioselectively to primary or secondary hydroxyls, i.e., $X_2$ and $X_3$, respectively. The amino group of chitosan can be protected for example with a phthalimido moiety, the primary hydroxyl with a triphenylmethyl moiety and the secondary hydroxyl with an acetyl moiety (Macromolecules 24, 1991, 4745). All of these protection groups can be conveniently cleaved and they enable the regioselective modification of chitosan (Macromolecules 24, 1991, 4745).

Starch, cellulose and other carbohydrate polymers containing hydroxyl groups can be converted to the quaternary polymer derivatives of the general formula (II) by esterification.

The esters can be prepared by reaction of a carbohydrate polymer with a reactive carboxyl derivative of the formula (V')

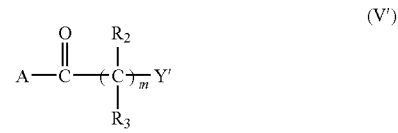

wherein A is any activating group and Y' is a suitable leaving group, e.g., chlorine, tosylate, iodine etc., preferably bromine or chlorine or is a quaternary ammonium group Y, $R_2$, $R_3$, m and Y are as hereinabove defined, and when a compound is obtained as an intermediate containing a leaving group Y', the intermediate is further reacted with a tertiary or aromatic amine corresponding to the group Y, to yield the desired quaternary polymer.

The reactive carboxyl derivatives of the formula (V') include acid chlorides (A=Cl), acid anhydrides (A=

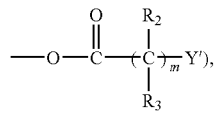

activated esters, activated amides. Acid anhydrides include symmetric anhydrides and mixed acid anhydrides. Active esters include p-nitrophenyl ester, ester with N-hydroxysuccinimide, etc. Activated amides include amide with imidazole. The carboxyl derivative can be activated using carbodiimides as activating agents, such as 1-ethyl-3-(3-dimethylaminopropyl) carbodiimide (EDC) or N,N'-dicyclohexylcarbodiimide (DCC). In this method, the carbohydrate polymer and the carboxyl derivative are mixed in an aqueous or non-aqueous solvent with the carbodiimide reagent. The carboxyl derivative is converted to the corresponding urea, which reacts with the basic hydroxyl groups of the carbohydrate polymer to form ester linkages, respectively.

The acid chlorides can be prepared with thionyl chloride, oxalyl chloride, phosphorus trichloride or phosphorus pentachloride in the presence of an excess of acid acceptor such as triethylamine in a non-polar solvent such as hexane, dichloromethane, toluene or benzene. The acid chloride may be isolated or it may be generated in situ.

Alternatively the carboxyl group can be activated with ethyl chloroformate in the presence of triethylamine to produce a mixed anhydride, and the latter is then reacted with the carbohydrate polymer to form amide or ester linkages.

When a carbohydrate polymer is reacted with the reactive carboxyl derivative shown in formula (V'), the intermediate containing the leaving group Y' is further reacted with a tertiary or aromatic amine corresponding to the group Y, preferably with 1,4-dimethylpiperazine, pyridine or 1-methylimidazole, to yield the quaternary polymer II.

For a review of modification of celluloses and starches, reference is made to Prog. Polym. Sci 26, 2001, 1689, and Robyt J: Polysaccharides II. Chemical modifications and their applications. Essential of Carbohydrate Chemistry. Pages 228-244. Springer-Verlag, New York, 1998

The following examples illustrate the invention, without limiting the same.

EXAMPLES

Characterization. $^1H$ and $^{13}C$ spectra were recorded on a Bruker AVANCE DRX 500, operating at 500.13 MHz and 125.76 MHz, respectively. Compounds were dissolved in $D_2O$ and 3-(Trimethylsilyl)propionate-$d_4$ was used as an internal standard. Measurements were carried out at 300 K or 343 K. $^1H$ and $^1H$ decoupled $^{13}C$ spectra were recorder in a routine way. For $^1H$ spectra, the recycling time was 4.6 s and 128 transients were collected. For $\{^1H\}$-$^{13}C$ spectra, the recycling time was 5.2 s and 8192 transients were accumulated. $^{13}C$-$^1H$ gradient-enhanced heteronuclear single quantum correlation (ge-HSQC) experiments were carried out in the phase sensitive mode, using the Echo/Antiecho-TPPI gradient selection. FT-IR spectra were recorded on a Nicolet 510 P spectrometer from KBr pellets.

Synthetic Procedures:

A previously reported method (Macromolecules 37, 2004, 2784) was used to convert chitosan into 6-O-triphenylmethylchitosan, via N-phthaloylchitosan and N-phthaloyl-6-O-triphenylmethylchitosan. 6-O-triphenylmethylchitosan (compound 4 in the examples) or N-chloroacyl-6-O-triphenylmethylchitosans (1 and 17 in the examples) were used as starting materials for the quaternization reactions. N-chloroacyl-6-O-triphenylmethylchitosans were prepared as described in Biomacromolecules 6, 2005, 858.

In the examples below, of the polymer formulas, only a reacting monomer unit is shown.

Example 1

N-[1-carboxymethyl-2-(1,4-dimethylpiperazinium)] chitosan chloride

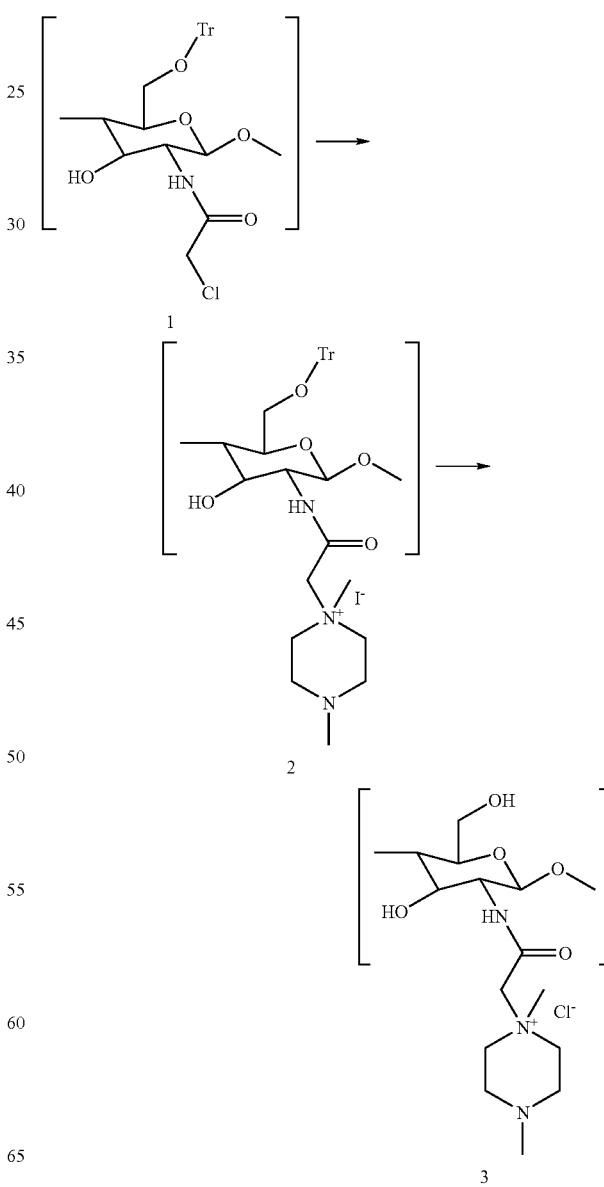

2.a) ds 0.4:1 g of N-chloroacetyl-6-O-triphenylmethylchitosan (1) (degree of N-chloroacetylation 0.4), 4.74 ml (35 mmol) 1,4-dimethylpiperazine and 232 mg (1.4 mmol) KI were stirred in 50 ml of N-methylpyrrolidone under argon at 60° C. for 72 h. The reaction mixture was cooled in ice-water and the product was precipitated with diethyl ether and washed with methanol and diethyl ether.

2.b) ds 0.46:1.4 g of N-chloroacetyl-6-O-triphenylmethylchitosan (1) (degree of N-chloroacetylation 0.46), 12.51 ml (92.5 mmol) 1,4-dimethylpiperazine and 0.614 g (3.7 mmol) KI were stirred in 70 ml of N-methylpyrrolidone under argon at 60° C. for 72 h. The reaction mixture was cooled in ice-water and the product was precipitated with diethylether and washed with methanol and diethyl ether.

2.c) ds 0.85:2 g of N-chloroacetyl-6-O-triphenylmethylchitosan (1) (degree of N-chloroacetylation 0.85), 24.3 ml (180 mmol) 1,4-dimethylpiperazine and 1.195 g (7.2 mmol) KI were stirred in 100 ml of N-methylpyrrolidone under argon at 60° C. for 72 h. The reaction mixture was cooled in ice-water and the product was precipitated with diethylether and washed with methanol and diethyl ether.

The 6-O-triphenylmethyl protection group was removed during a 3-hour reaction by stirring compounds 2a-c with 1M HCl at room temperature. The reaction mixture was evaporated to dryness and the product was washed with methanol and diethyl ether. Products were dialyzed against water at room temperature for 24 h and then freeze-dried (ThermoSavant ModulyoD-230, Savant, Holbrook, N.Y.).

3.a) 730 mg of 2a yielded 360 mg of 3a (94%). Degree of substitution determined by $^1$H NMR was 0.40.

3.b) 960 mg of 2b yielded 387 mg of 3b (76%). Degree of substitution determined by $^1$H NMR was 0.46.

3.c) 1.35 g of 2c yielded 720 mg of 3c (96%). Degree of substitution determined by $^1$H NMR was 0.85.

IR (KBr): ν 3600-3100 (O—H), 3000-2700 (C—H), 1682 (amide I), 1565 (amide II), 1470 (C—N), 1150-950 cm$^{-1}$ (C—O, pyranose). $^1$H NMR at 343K (D$_2$O): δ 2.0 (CH$_3$, N-acetyl), 2.4 (H-11), 2.8-3.0 (H-10), 3.0-3.1 (H-2, when amino group unsubstituted), 3.3-3.4 (H-12), 3.4-3.9 (H-9, H-6, H-5, H-4, H-3, H-2 substituted), 4.2 (H-8), 4.6-4.8 ppm (H-1). $^{13}$C NMR at 343K (D$_2$O): δ 25.0 (CH$_3$, N-acetyl), 46.5 (C-11), 50.3 (C-10), 51.4 (C-12), 58.4 (C-2, substituted), 59.1 (C-2, unsubstituted), 63.1 (C-6, substituted), 63.3 (C-6, unsubstituted), 63.8 (C-9), 63.9 (C-9), 65.3 (C-8), 74.7 (C-3), 77.7 (C-5), 80.5 (C-4 unsubstituted), 81.4 (C-4, substituted), 102.9 (C-1, substituted), 104.0 (C-1, unsubstituted), 167.0 (C-7), 177.1 ppm (C=O, N-acetyl).

Example 2

N-[1-carboxymethyl-2-(4,4-dimethylpiperazinium)] chitosan chloride

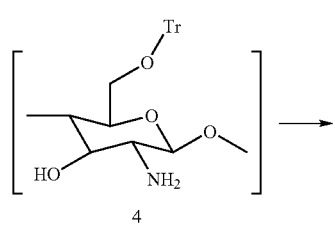
4

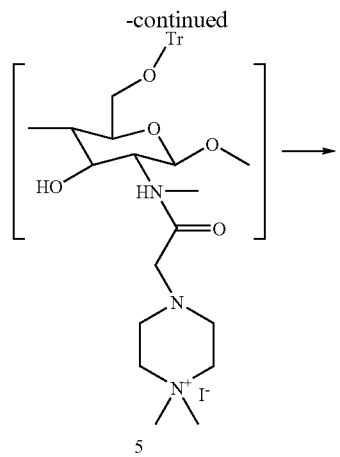
5

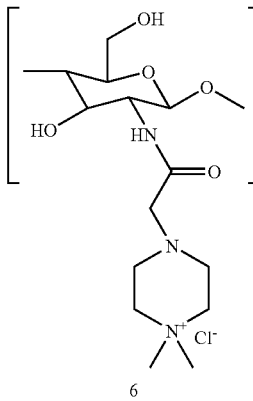
6

The preparation of 4-carboxymethyl-1,1-dimethylpiperazinium iodide is described in example 9. General procedure. 1 g of 6-O-triphenylmethylchitosan (4) (free amino group content 2.074 mmol) was dissolved in 50 mL of N-methylpyrrolidone. 4-carboxymethyl-1,1-dimethylpiperazinium iodide, 1-hydroxybenzotriazole and N,N'-dicyclohexylcarbodiimide were dissolved in 20 mL of N-methylpyrrolidone. The solutions were combined and stirred at room temperature under argon for 96 h. The products were precipitated with diethyl ether and washed with methanol and diethyl ether.

5.a) Amounts of reagents used: 214 mg (0.713 mmol) 4-carboxymethyl-1 μl-dimethylpiperazinium iodide (0.34 equiv), 110 mg (0.814 mmol, 0.39 equiv) 1-hydroxybenzotriazole and 171 mg (0.829 mol, 0.40 equiv) N,N'-dicyclohexylcarbodiimide. 674 mg (61%) of product 5a was obtained.

5.b) Amounts of reagents used: 410 mg (1.366 mmol, 0.66 equiv) 4-carboxymethyl-1,1-dimethylpiperazinium iodide, 219 mg (1.620 mmol, 0.78 equiv) 1-hydroxybenzotriazole and 337 mg (1.633 mmol, 0.79 equiv) N,N'-dicyclohexylcarbodiimide. 897 mg (70%) of product 5b was obtained.

5.c) Amounts of reagents used: 828 mg (2.759 mmol, 1.33 equiv) 4-carboxymethyl-1,1-dimethylpiperazinium iodide, 447 mg (3.241 mmol, 1.56 equiv) 1-hydroxybenzotriazole and 677 mg (3.281 mmol, 1.582 equiv) N,N'-dicyclohexylcarbodiimide. 1.714 g (100%) of product 5c was obtained.

The 6-O-triphenylmethyl protection group was removed during a 3-hour reaction by stirring compounds 5a-c with 1M HCl at room temperature. Reaction mixture was evaporated to dryness and product was washed with methanol and diethyl ether. Products were dialyzed against water at room temperature for 24 h and then freeze-dried (ThermoSavant Modulyo D-230, Savant, Holbrook, N.Y.).

6.a) 650 mg of 5a yielded 269 mg of 6a (82%). Degree of substitution determined by $^1$H NMR was 0.15.

6.b) 880 mg of 5b yielded 329 mg of 6b (71%). Degree of substitution determined by $^1$H NMR was 0.42.

6.c) 1.61 g of 5c yielded 550 mg of 6c (61%). Degree of substitution determined by $^1$H NMR was 0.87.

IR (KBr): ν 3600-3100 (O—H), 3000-2700 (C—H), 1658 (amide I), 1534 (amide II), 1475 (C—N), 1150-950 cm$^{-1}$ (C—O, pyranose). $^1$H NMR at 343K (D$_2$O): δ 2.0 (CH$_3$, N-acetyl), 2.9-3.0 (H-9), 3.0-3.1 (H-2, when amino group unsubstituted), 3.1-3.2 (H-11, H-12), 3.25-3.5 (H-8), 3.45-3.8 (H-10), 3.5-3.7 (H-5), 3.6-4.0 (H-6), 3.55-3.7 (H-4, substituted), 3.6-3.8 (H-3), 3.7-3.9 (H-2, substituted), 3.75-3.9 (H-4, unsubstituted), 4.6-4.8 ppm (H-1). $^{13}$C NMR at 343K (D$_2$O): δ 25.0 (CH$_3$, N-acetyl), 49.0 (C-9), 54.4 (C-11, C-12), 58.0 (C-2, substituted), 59.1 (C-2, unsubstituted), 61.9 (C-8), 63.0 (C-6, substituted), 63.3 (C-6, unsubstituted), 64.3 (C-10), 74.3 (C-3, unsubstituted), 74.7 (C-3, substituted), 77.4 (C-5, substituted), 77.7 (C-5, unsubstituted), 80.9 (C-4 unsubstituted), 81.8 (C-4, substituted), 102.1 (C-1, unsubstituted), 103.4 (C-1, substituted), 175.2 (C-7), 177.2 ppm (C=O, N-acetyl).

Example 3

N-[1-carboxymethyl-2-(1,4,4-trimethylpiperazi-1,4-dium)]chitosan dichloride

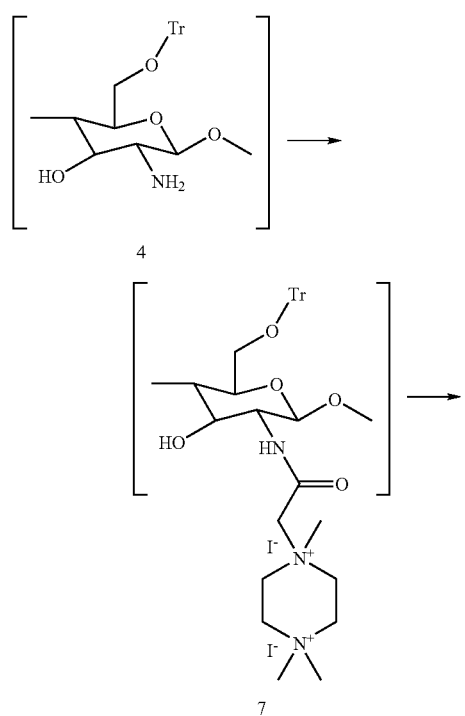

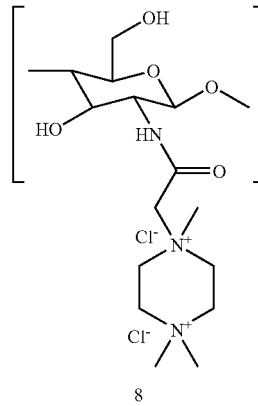

The preparation of 1-carboxymethyl-1,4,4-trimethylpiperazi-1,4-dium diiodide is described in example 9. General procedure. 1 g of 6-O-triphenylmethylchitosan (4) (free amino group content 2.074 mmol) was dissolved in 50 mL of N-methylpyrrolidone. 1-carboxymethyl-1,4,4-trimethylpiperazi-1,4-dium diiodide, 1-hydroxybenzotriazole and N,N'-dicyclohexylcarbodiimide were dissolved in 20 mL of N-methylpyrrolidone. The solutions were combined and stirred at room temperature under argon for 96 h. The products were precipitated with diethyl ether and washed with methanol and diethyl ether.

7.a) Amounts of reagents used: 473 mg (1.07 mmol) 1-carboxymethyl-1,4,4-trimethylpiperazi-1,4-dium diiodide (0.52 equivalents compared to free amino group in 6-O-triphenylmethylchitosan), 173 mg (1.28 mmol, 0.62 equiv) 1-hydroxybenzotriazole and 264 mg (1.28 mmol, 0.62 equiv) N,N'-dicyclohexylcarbodiimide. 1.08 g (87%) of product 7a was obtained.

7.b) Amounts of reagents used: 941 mg (2.13 mmol, 1.03 equiv) 1-carboxymethyl-1,4,4-trimethylpiperazi-1,4-dium diiodide, 346 mg (2.56 mmol, 1.23 equiv) 1-hydroxybenzotriazole and 528 mg (2.56 mmol, 1.23 equiv) N,N'-dicyclohexylcarbodiimide. 1.29 g (93%) of product 7b was obtained.

7.c) Amounts of reagents used: 1.883 mg (4.26 mmol, 2.05 equiv) 1-carboxymethyl-1,4,4-trimethylpiperazi-1,4-dium diiodide, 691 mg (5.11 mmol, 2.46 equiv) 1-hydroxybenzotriazole and 1.054 g (5.11 mmol, 2.46 equiv) mg N,N'-dicyclohexylcarbodiimide. 1.71 g (100%) of product 7c was obtained.

The 6-O-triphenylmethyl protection group was removed during a 3-hour reaction by stirring compounds 7a-c with 1M HCl at room temperature. Reaction mixture was evaporated to dryness and product was washed with methanol and diethyl ether. Products were dialyzed against water at room temperature for 24 h and then freeze-dried (ThermoSavant Modulyo D-230, Savant, Holbrook, N.Y.).

8.a) 1.08 g of 7a yielded 460 mg of 8a (81%). Degree of substitution determined by $^1$H NMR was 0.34.

8.b) 1.29 g of 7b yielded 590 mg of 8b (84%). Degree of substitution determined by $^1$H NMR was 0.54.

8.c) 1.71 g of 7c yielded 640 mg of 8c (68%). Degree of substitution determined by $^1$H NMR was 0.65.

IR (KBr): ν 3600-3100 (O—H), 3000-2700 (C—H), 1682 (amide I), 1563 (amide II), 1481 (C—N), 1150-950 cm$^{-1}$ (C—O, pyranose). $^1$H NMR at 343K (D$_2$O): δ 2.0 (CH$_3$, N-acetyl), 3.0-3.1 (H-2, when amino group unsubstituted), 3.4-3.6 (H-11, H-12), 3.5-3.6 (H-13), 3.55-3.8 (H-5), 3.6-4.0 (H-6), 3.6-3.9 (H-4), 3.65-3.8 (H-3), 3.7-4.5 (H-9, H-10), 3.7-3.8 (H-2, substituted), 4.3-4.4 (H-8), 4.6-4.8 ppm (H-1). $^{13}$C NMR at 343K (D$_2$O): δ 25.0 (CH$_3$, N-acetyl), 52.0 (C-13), 53.7 (C-11), 56.9 (C-12), 57.9 and 58.1 (C-9), 58.4 (C-10), 58.9 (C-2, substituted), 59.0 (C-2, unsubstituted), 63.4 (C-6), 65.6 (C-8), 63.3, 74.4 (C-3), 77.7 (C-5), 80.9 (C-4), 102.2 (C-1, unsubstituted), 102.8 (C-1, substituted), 166.5 (C-7), 177.1 ppm (C=O, N-acetyl).

Example 4

N-(1-carboxymethyl-2-pyridinium)chitosan chloride

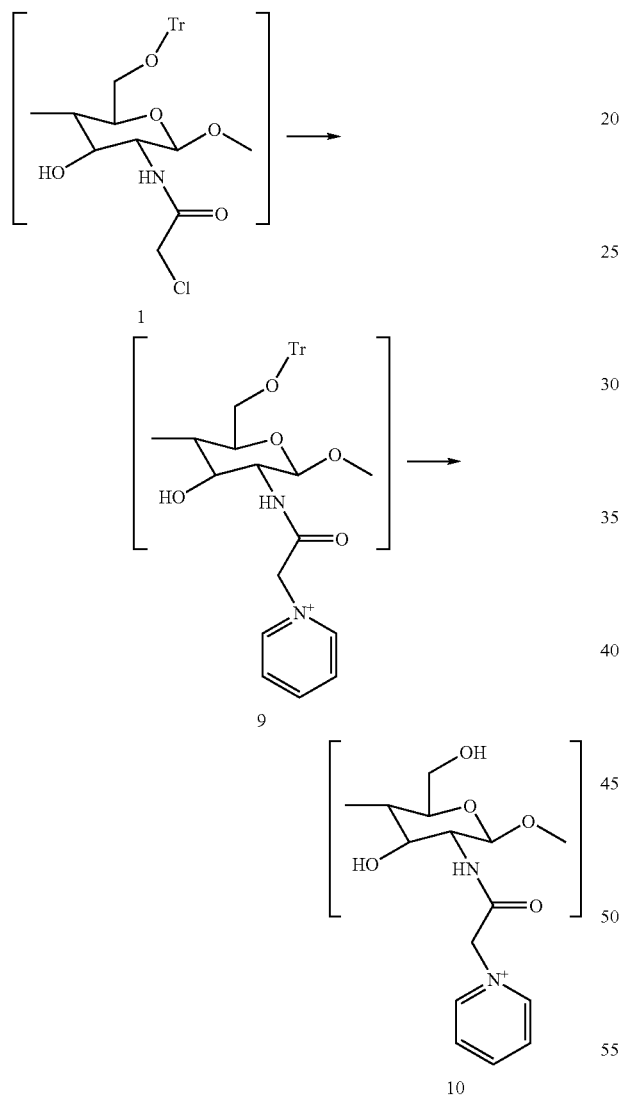

300 mg of N-chloroacetyl-6-O-triphenylmethylchitosan (1) (degree of N-chloroacetylation 0.85) was stirred in 10 ml of pyridine under argon at 60° C. for 72 h. The solvent was evaporated and the product was washed with methanol and diethyl ether. The relative yield of product 9 was 176 mg (51%).

The 6-O-triphenylmethyl protection group was removed during a 3-hour reaction by stirring 170 mg of compound 9 with 20 ml of 1M HCl at room temperature. The reaction mixture was evaporated to dryness and the product was washed with methanol and diethyl ether. The degree of substitution calculated from $^1$H NMR spectra was 0.85. The yield of the product (10) was 63 mg (65%). IR (KBr): ν 3600-3100 (O—H), 3100-3000 (C—H, pyridyl), 2950-2700 (C—H), 1687 (amide I), 1559 (amide II), 1490 (C=C, pyridyl), 1374 (C=C, pyridyl), 1150-950 (C—O, pyranose), 783 (arom, pyridyl), 725 (arom, pyridyl), 677 cm$^{-1}$ (arom, pyridyl). $^1$H NMR at 300K (D$_2$O): δ 2.0 (CH$_3$, N-acetyl), 3.5-3.6 (H-5), 3.7-4.0 (H-6), 3.7-3.8 (H-4), 3.8-4.0 (H-3), 3.85-4.0 (H-2), 4.7-4.8 (H-1), 5.5-5.7 (H-8), 8.1-8.2 (H-10), 8.65-8.75 (H-11), 8.75-8.9 ppm (H-9). $^{13}$C NMR at 300K (D$_2$O): δ 25.0 (CH$_3$, N-acetyl), 58.8 (C-2), 63.0 (C-6), 64.6 (C-8), 74.7 (C-3), 77.6 (C-5), 81.1 (C-4), 103.3 (C-1), 131.0 (C-10), 148.6 (C-9), 149.8 (C-11) 169.4 ppm (C-7).

Example 5

N-[1-carboxymethyl-2(1-methylimidazolium)]chitosan chloride

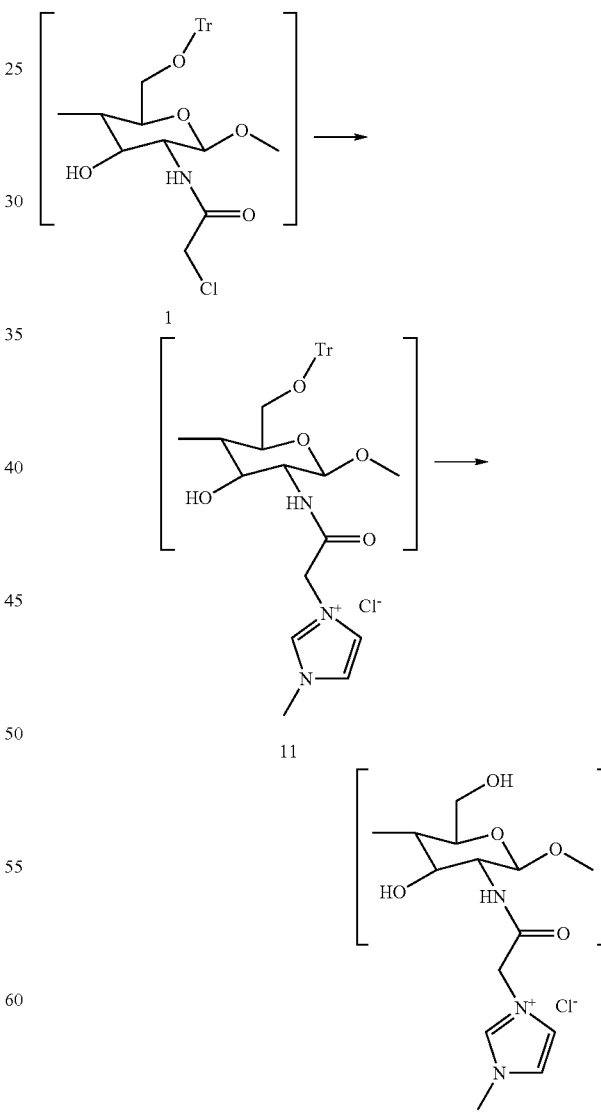

295 mg of N-chloroacetyl-6-O-triphenylmethylchitosan (1) (degree of N-chloroacetylation 0.85) was stirred in 10 ml of 1-methylimidazole under argon at 60° C. for 72 h. The reaction mixture was evaporated to dryness and the product was washed with methanol and diethyl ether. The relative yield of product 11 was 116 mg (34%).

The 6-O-triphenylmethyl protection group was removed during a 3-hour reaction by stirring 105 mg of compound 11 with 15 ml of 1M HCl at room temperature. The reaction mixture was evaporated to dryness and the product was washed with methanol and diethyl ether. The degree of substitution calculated from $^1$H NMR spectra was 0.85. The yield of the product (12) was 45 mg (77%). IR (KBr): ν 3600-3100 (O—H), 3100-3000 (C—H, imidazole), 2950-2700 (C—H), 1685 (amide I), 1560 (amide II), 1375 (C=C, imidazole), 1150-950. $^1$H NMR at 300K (D$_2$O): δ 2.1 (CH$_3$, N-acetyl), 3.5-3.6 (H-5), 3.6-3.9 (H-6), 3.6-3.8 (H-4), 3.7-3.9 (H-3), 3.8-3.9 (H-2), 3.9-4.0 (H-12), 4.6-4.8 (H-1), 5.1-5.3 (H-8), 7.50 (H-11), 7.52 (H-10), 8.75-8.85 ppm (H-9). $^{13}$C NMR at 300K (D$_2$O): δ 25.0 (CH$_3$, N-acetyl), 38.8 (C-12), 53.6 (C-8), 58.6 (C-2), 63.0 (C-6), 74.7 (C-3), 77.6 (C-5), 81.3 (C-4), 103.4 (C-1), 126.3 (C-11), 126.5 (C-10), 140.3 (C-9) 170.5 ppm (C-7).

Example 6

N-(1-carboxybutyl-4-pyridinium)chitosan chloride

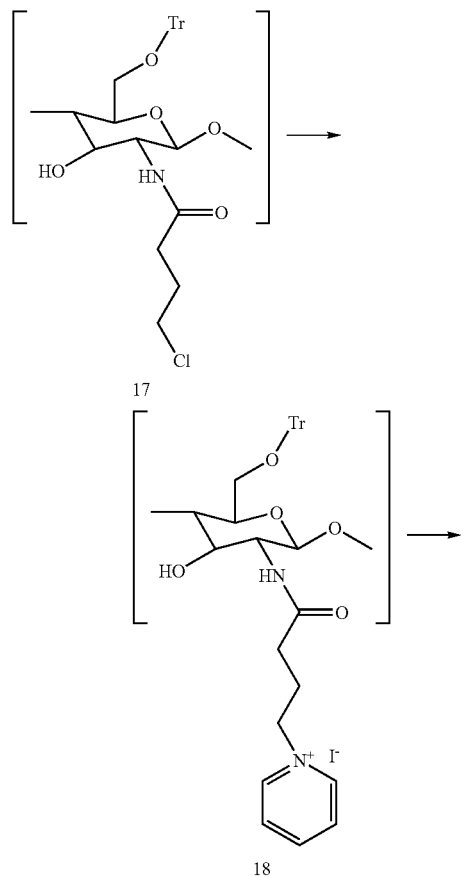

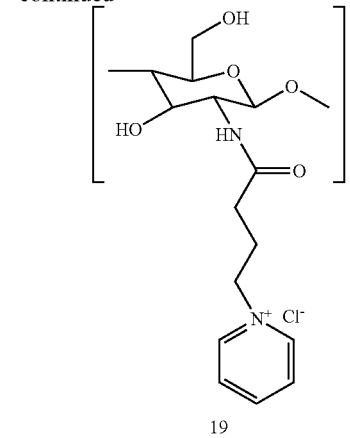

220 mg of N-chlorobutyryl-6-O-triphenylmethylchitosan (17) (degree of N-chlorobutyrylation 0.67) was stirred in 8 ml of pyridine under argon at 60° C. for 72 h. The solvent was evaporated and the product was washed with methanol and diethyl ether. The relative yield of 18 was 140 mg (57%).

The 6-O-triphenylmethyl protection group was removed during a 3-hour reaction by stirring 140 mg of compound 18 with 14 ml of 1M HCl at room temperature. The reaction mixture was evaporated to dryness and the product was washed with methanol and diethyl ether. The degree of substitution of 19 calculated from $^1$H NMR spectra was 0.67. The yield of the product (19) was 44 mg (56%). IR (KBr): ν 3600-3100 (O—H), 3000-2700 (C—H), 1655 (amide I), 1554 (amide II), 1489 (C=C), 1150-950 cm$^{-1}$ (C—O, pyranose). $^1$H NMR at 343K (D$_2$O): δ 2.0 (CH$_3$, N-acetyl), 2.3-2.4 (H-9), 2.4-2.5 (H-8), 3.1-3.2 (H-2, when amino group unsubstituted), 3.4-3.9 (H-6, H-5, H-4, H-3, H-2 substituted), 4.5-4.6 (H-1, substituted), 4.6-4.7 (H-10), 4.8-4.9 (H-1, unsubstituted), 8.1-8.2 (H-12), 8.5-8.6 (H-13), 8.8-8.9 ppm (H-11). $^{13}$C NMR at 343K (D$_2$O): δ 25.1 (CH$_3$, N-acetyl), 29.1 (C-9), 34.8 (C-8), 58.2 (C-2, substituted), 58.8 (C-2, unsubstituted), 63.2 (C-6, substituted), 63.4 (C-6, unsubstituted), 63.7 (C-10), 73.5 (C-3, unsubstituted), 74.9 (C-3, substituted), 77.6 (C-5, substituted), 78.1 (C-5, unsubstituted), 80.2 (C-4 unsubstituted), 82.2 (C-4, substituted), 100.5 (C-1, unsubstituted), 103.8 (C-1, substituted), 131.3 (C-12), 147.0 (C-13), 148.8 (C-11), 177.3 (C-7).

Example 7

Quaternary Piperazinium Acids

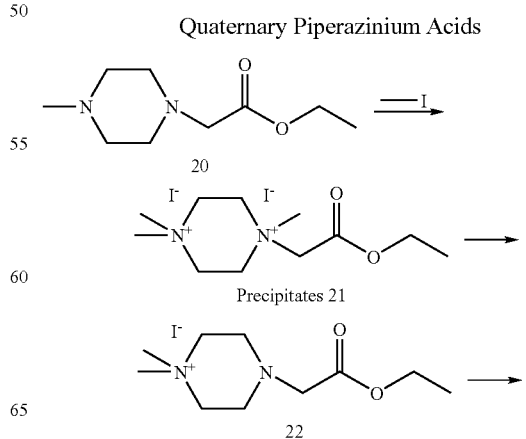

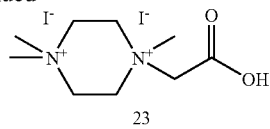

23

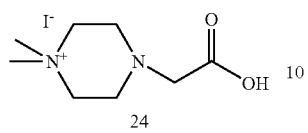

24

1-(2-ethoxy-2-oxoethyl)-4-methylpiperazine (20) was prepared from 1-methylpiperazine and ethylbromoacetate as described in Journal of Medicinal Chemistry 43, 2000, 1489. When the compound 20 was reacted with MeI in dry acetonitrile, 1-(2-ethoxy-2-oxoethyl)-1,4,4-trimethylpiperazi-1,4-dium diiodide (21) precipitated as a pure compound and 4-(2-ethoxy-2-oxoethyl)-1,1-dimethylpiperazinium iodide (22) remained in solution. 6.96 g (37.37 mmol) of 1-(2-ethoxy-2-oxoethyl)-4-methylpiperazine (20) and 9.3 ml (149 mmol, 4 equiv) of MeI were reacted in 270 ml of ACN for 48 h. The precipitate was filtered and washed with acetonitrile. The precipitate yielded 2.354 g (13%) of 1-(2-ethoxy-2-oxoethyl)-1,4,4-trimethylpiperazi-1,4-dium diiodide (21). The filtrate was evaporated to dryness and the yield of 4-(2-ethoxy-2-oxoethyl)-1,1-dimethylpiperazinium iodide (22) was 9.998 g (82%). This reaction was repeated with 7.8 g (41.9 mmol) of 1-(2-ethoxy-2-oxoethyl)-4-methylpiperazine (20) and 26.1 mL (420 mmol, 10 equiv) of MeI. The reaction was proceeded in 300 ml ACN for 240 h. The precipitate was filtered and washed with acetonitrile. The precipitate yielded 11.124 g (57%) of 1-(2-ethoxy-2-oxoethyl)-1,4,4-trimethylpiperazi-1,4-dium diiodide (21). The filtrate was evaporated to dryness and the yield of 4-(2-ethoxy-2-oxoethyl)-1,1-dimethylpiperazinium iodide (22) was 5.82 g (42.2%).

1-(2-ethoxy-2-oxoethyl)-1,4,4-trimethylpiperazi-1,4-dium diiodide (21): $^1$H NMR at 300K (D$_2$O): δ 1.33 (2H, t, J=14 Hz), 3.44 (3H, s), 3.47 (3H, s), 3.59 (3H, s), 3.9-4.3 (8H, bm), 4.37 (2H, q, J=14 Hz), 4.67 (2H, d)

$^{13}$C NMR at 343K (D$_2$O): δ 16.03, 51.89, 53.60, 57.01, 57.75 (2C), 58.27 (2C), 58.49, 67.08, 167.03

4-(2-ethoxy-2-oxoethyl)-1,1-dimethylpiperazinium iodide (22): $^1$H NMR at 300K (D$_2$O): δ 1.28 (2H, t, J=14 Hz), 3.01 (4H, s), 3.21 (6H, s), 3.49 (4H, s), 3.51 (2H, s), 4.24 (2H, q, J=14 Hz)

$^{13}$C NMR at 343K (D$_2$O): δ 16.18, 48.58 (2C), 54.50 (2C), 60.04 (2C), 64.25, 64.98, 174.44

The ethyl ester groups were cleaved by refluxing the compounds 21 and 22 in water.

1-carboxymethyl-1,4,4-trimethylpiperazi-1,4-dium diiodide (23). 8.5 g of 1-(2-ethoxy-2-oxoethyl)-1,4,4-trimethylpiperazi-1,4-dium diiodide (21) was refluxed in 700 ml water for 96 h. The reaction mixture was evaporated to dryness and the procedure was repeated. The product was washed with acetone and crystallized with ethanol from water. Yielded white powder 4.98 g (62%). $^1$H NMR at 300K (D$_2$O): δ 3.41 (3H, s), 3.43 (3H, s), 3.49 (3H, s), 3.9-4.1 (6H, bm), 4.35 (2H, s), 4.4-4.5 (2H, bm)

$^{13}$C NMR at 343K (D$_2$O): δ 51.79, 53.45, 56.85 (3C), 58.44 (2C), 66.58, 169.53

4-carboxymethyl-1,1-dimethylpiperazinium iodide (24). 11.77 g of 4-(2-ethoxy-2-oxoethyl)-1,1-dimethylpiperazinium iodide (22) was refluxed in 600 ml water for 48 h. The reaction mixture was evaporated to dryness and the product was crystallized with diethyl ether from ethanol. Yielded white powder 5.484 g (51%). $^1$H NMR at 300K (D$_2$O): δ 3.30 (6H, s), 3.51 (4H, s), 3.69 (2H, s), 3.73 (4H, bm)

$^{13}$C NMR at 343K (D$_2$O): δ 48.86 (2C), 54.84 (2C), 60.47, 62.74 (2C), 173.72

The invention claimed is:

1. Quaternary polymers having a general formula:

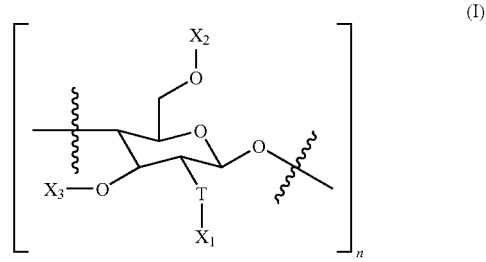

(I)

wherein
T is NH or O,
$X_1$, $X_2$ and $X_3$ are independently:
H or a quaternary substituent

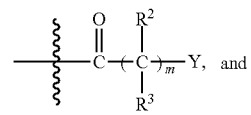

in the case of T being NH (i.e., chitin and chitosan), $X_1$, $X_2$ and $X_3$ can also be a quaternary substituent

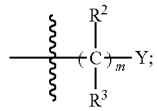

and, in addition, $X_1$ can also be:
H or

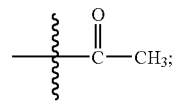

wherein $R_2$ and $R_3$ are independently H or a linear or branched, substituted or unsubstituted alkyl chain with 1 to 6 carbon atoms and m is an integer from 1 to 12, and
wherein Y is a quaternary ammonium moiety, selected from piperazine moieties having the formula (A)

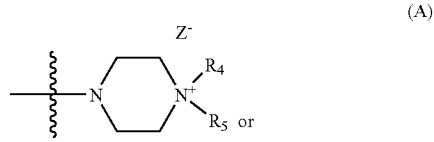

(B)

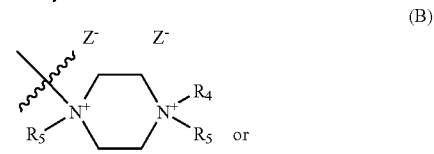

-continued

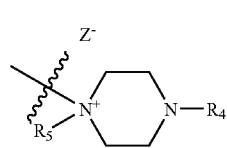
(C)

or selected from the groups

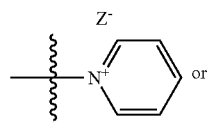
(D)

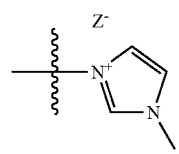
(E)

wherein $R_4$ and $R_5$ are independently a linear or branched, substituted or unsubstituted alkyl chain with 1 to 6 carbon atoms, $Z^-$ is a negatively charged counter ion, whereby the degree of substitution (ds) of the quaternary substituent in the polymer structure for the total of the groups $X_1$, $X_2$ and $X_3$ is from 0.01 to 3, n is the degree of polymerization, and can be an integer from 2 to 100000, with the proviso that when T is O, Y can only have the meaning of the formula (A), (B), (C) or (E).

2. The polymers according to claim 1, wherein T is NH, and Y is one of the formulas (A), (B) or (C), wherein the degree of substitution of the quaternary substituent is from 0.01 to 1.

3. The polymers according to claim 2, wherein the degree of substitution of the quaternary substituent is from 0.05 to 1.

4. The polymers according to claim 1, wherein T is NH, $X_2$ and $X_3$ are hydrogen and $X_1$ is hydrogen, acetyl or the quaternary substituent, and the degree of substitution of the quaternary substituent is from 0.01 to 1.

5. The polymers according to claim 4, wherein $X_1$ is the quaternary substituent.

6. The polymers according to claim 4, wherein $X_1$ is one of the quaternary substituents wherein Y has one of the formulas (A), (B) or (C).

7. The polymers according to claim 4, wherein the degree of substitution of the quaternary group substituent is from 0.05 to 1.

8. The polymers according to claim 1, wherein the degree of substitution of the quaternary substituent is from 0.05 to 1.

9. The polymers according to claim 1, wherein T is O, $X_1$, $X_2$, and $X_3$ are hydrogen or the quaternary substituent wherein Y is one of the formulas (A), (B), (C) or (E), and wherein the degree of substitution of the quaternary substituent is from 0.01 to 1.

10. The polymers according to claim 1, wherein $Z^-$ is a negatively charged counter ion selected from the group consisting of $Cl^-$, $Br^-$, $I^-$, $OH^-$, $R_1COO^-$, $R_1SO_4^-$, wherein $R_1$ is H or an alkyl group with 1 to 6 carbon atoms or an aromatic moiety.

11. A process for the preparation of the quaternary polymers according to the formula (I) in claim 1, the process comprising:

I. for the preparation of a compound wherein T is NH:
a) reacting a chitin or chitosan derivative having a free amino or hydroxyl group, and wherein the remaining reactive groups are optionally in protected form, with
(i) a compound having the formula V'

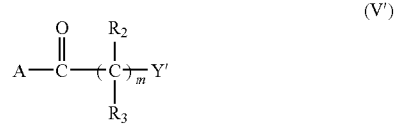
(V')

wherein A is an activating group, Y' is a suitable leaving group or is a quaternary ammonium moiety Y, $R_2$, $R_3$, m and Y are as above defined, or (ii) with a compound having the formula III

(III)

wherein L is a leaving group, and Y' is either a quaternary ammonium-group moiety Y or a suitable leaving group, and $R_2$, $R_3$, m and Y are as above defined, whereby L is as good as or better than or is a more reactive leaving group as compared to the leaving group Y', and when an intermediate compound containing a leaving group Y' is obtained, the intermediate compound is further reacted with a tertiary or aromatic amine corresponding to the quaternary ammonium moiety Y, to yield the desired quaternary polymer, and then removing any protecting groups; or b) for the preparation of a chitin or chitosan derivative having an amino group substituted with a group $X_1$ containing a quaternary ammonium moiety Y, and $X_2$ and $X_3$ are hydrogen, reacting a chitin or chitosan polymer in which the hydroxyl groups in the 3 and/or 6-positions are optionally protected, and the amino group in one or more of the monomer units of the polymer carries an alkyl or alkyloxy group corresponding to the group $X_1$, wherein the moiety Y is replaced by a suitable leaving group, with a tertiary or aromatic amine corresponding to the quaternary ammonium moiety Y, and removing any protecting groups; or c) for the preparation of a chitin or chitosan derivative having an amino group substituted with a group $X_1$ containing a quaternary ammonium group, reacting a chitin or chitosan polymer having a free amino group and in which the hydroxyl groups in the 3 and/or 6-positions are optionally protected, with a compound having the formula III or V' as defined above, and when Y' in the formula III or V' is a leaving group, reacting the so obtained intermediate compound with a tertiary or aromatic amine corresponding to the moiety Y, and removing any protecting groups, whereby a compound obtained wherein $X_1$, $X_2$ and/or $X_3$ have the meaning of hydrogen, can be converted to a compound wherein said $X_1$, $X_2$ and/or $X_3$ are different from hydrogen, by reacting the same with a compound of the formula III or V' as defined above, and reacting an intermediate so obtained containing a leaving group Y', with a tertiary or aromatic amine corresponding to the quaternary ammonium group Y, and removing any protecting groups optionally used in the reaction; or II. for the preparation of a compound wherein T is O: esterifying a carbohydrate polymer containing at least one unprotected hydroxyl group with a reactive carboxyl derivative having the formula

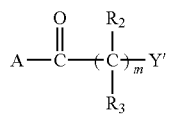

(V')

wherein A is an activating group, Y' is a suitable leaving group or a quaternary ammonium moiety Y, $R_2$, $R_3$, m and Y are as above defined, and when a compound is obtained as an intermediate containing a leaving group Y', the intermediate is further reacted with a tertiary or aromatic amine corresponding to the moiety Y, to yield the desired quaternary polymer, and removing any protecting group from a compound obtained, and, if desired, converting a compound obtained wherein $X_1$, $X_2$ and/or $X_3$ is hydrogen, to a compound wherein $X_1$, $X_2$ and/or $X_3$ is different from hydrogen, by reacting with a compound of the formula V', and in case a compound containing a leaving group is obtained as an intermediate, reacting the intermediate with a tertiary or aromatic amine corresponding to the quaternary ammonium group moiety Y, and removing any protecting groups optionally used in the reaction.

* * * * *